| United States Patent [19] | [11] Patent Number: 4,581,454 |
| Myers et al. | [45] Date of Patent: *Apr. 8, 1986 |

[54] ADDUCTS OF AMINOHYDROCARBYL PIPERZAINES AND UREA

[75] Inventors: Jimmy Myers, Sweeny; William P. Coker, Lake Jackson, both of Tex.

[73] Assignee: The Dow Chemical Company, Midland, Mich.

[*] Notice: The portion of the term of this patent subsequent to Oct. 16, 2001 has been disclaimed.

[21] Appl. No.: 514,761

[22] Filed: Jul. 18, 1983

[51] Int. Cl.$^4$ .................. C07D 403/12; C07D 403/14
[52] U.S. Cl. .................................. 544/357; 544/400; 544/39 D
[58] Field of Search ...................... 544/357, 400, 39 D

[56] References Cited

U.S. PATENT DOCUMENTS

| 2,379,261 | 6/1945 | Strain | 260/463 |
| 4,178,426 | 12/1979 | Waddill | 525/307 |
| 4,239,761 | 12/1980 | Rebling et al. | 424/250 |
| 4,477,646 | 10/1984 | Myers | 528/118 |
| 4,490,510 | 12/1984 | Cummings | 525/510 X |

Primary Examiner—Donald G. Daus
Assistant Examiner—William A. Teoli, Jr.
Attorney, Agent, or Firm—J. G. Carter

[57] ABSTRACT

Adducts of aminohydrocarbyl piperazines and urea are prepared in the presence of basic catalysts. These adducts are useful as curing agents for epoxy resins.

11 Claims, No Drawings

ADDUCTS OF AMINOHYDROCARBYL PIPERZAINES AND UREA

BACKGROUND OF THE INVENTION

In order to provide epoxy resin systems for reaction injection molding (RIM) applications, it is desirable that a favorable mix ratio between the epoxy resin and hardener be obtained. Such a favorable mix ratio, by weight, of epoxy resin to hardener is considered to be from about 1:1 to about 1.5:1. The usual amine hardeners such as, for example, ethylenediamine, diethylenetriamine, methylenediamine, hydrogenated methylenediamine, have amine hydrogen equivalent weights of from about 15 to about 53 which provide epoxy to hardener mix ratios of from about 3.4:1 to about 12:1.

In RIM epoxy systems, a considerable quantity of a trifunctional epoxy resin may be employed to provide a crosslinked network to the cured polymer. Since these trifunctional epoxides are usually solid resins, they must be heated before mixing with the hardener. It is therefore desirable that the viscosities of these epoxides and the curing agent or hardener be compatible at the mix temperature.

It has now been discovered that the compositions of the present invention provide more suitable mix ratios thereby lending them particularly suitable for epoxy RIM applications as well as conventional epoxy applications.

SUMMARY OF THE INVENTION

The present invention pertains to the uncrystallized reaction product of (A) at least one aminohydrocarbyl piperazine and (B) urea in a mole ratio of (A) to (B) of from about 1.8:1 to about 8:1, preferably from about 1.8:1 to about 2.2:1 and wherein said uncrystallized reaction product has an amine hydrogen equivalent weight determined by titration with HCl of at least about 110, preferably from about 130 to about 210.

The present invention also pertains to aminohydrocarbyl piperazine-urea adducts represented by the general formula

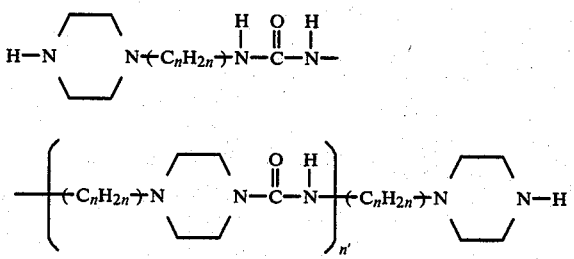

wherein each n is independently an integer from 2 to about 10, preferably from about 2 to about 4, most preferably from about 2 to about 3; and n' has an average value of from about zero to about 2.

The present invention also pertains to a process for preparing uncrystallized adducts of aminoalkyl piperazines and urea which process comprises (1) adding (A) urea to (B) an excess of at least one aminohydrocarbyl piperazine optionally in the presence of (C) a catalytic quantity of a catalyst for effecting the reaction between (A) and (B) and at a temperature for effecting the reaction between (A) and (B) for a time sufficient to substantially complete the reaction and (2) recovering the uncrystallized adducts produced by the reaction between (A) and (B).

The present invention also pertains to the cured reaction product of (1) at least one epoxy resin having an average of more than one vicinal epoxy group per molecule and (2) a curing quantity of an uncrystallized adduct formed by the reaction of (A) at least one aminohydrocarbyl piperazine and (B) urea, said adduct having an amine hydrogen equivalent weight determined by titration with HCl using brom thymol blue as the indicator of at least about 110, preferably from about 30 to about 200.

DETAILED DESCRIPTION OF THE INVENTION

Suitable aminoalkyl piperazines which can be employed herein include those represented by the general formula

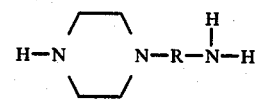

wherein R is a divalent hydrocarbyl group having from about 2 to about 10, preferably from about 2 to about 4, and most preferably from about 2 to about 3 carbon atoms. The hydrocarbon group can be cyclic, acyclic, aromatic or non-aromatic. Particularly suitable aminohydrocarbyl piperazines include, for example, aminoethyl piperazine, aminopropyl piperazine, aminobutyl piperazine, aminopentyl piperazine, aminohexyl piperazine, aminoheptyl piperazine, aminooctyl piperazine, aminononyl piperazine, aminodecyl piperazine, mixtures thereof and the like.

Suitable catalysts which can be employed include such basic catalysts as, for example, basic ion exchange resins, quaternary ammonium compounds, phosphonium compounds, imidazoles, mixtures thereof and the like.

Suitable basic ion exchange resins include, for example, DOWEX MSA-1 (chloride or hydroxide form), DOWEX 1, DOWEX 2, DOWEX 11, DOWEX 21K, mixtures thereof and the like.

The ion exchange resin can be employed either in the wet or dry form.

Suitable quaternary ammonium catalyst include, for example, benzyltrimethylammonium chloride, benzyltrimethylammonium bromide, benzyltrimethylammonium hydroxide, tetramethylammonium chloride, tetramethylammonium bromide, tetramethylammonium hydroxide, tetrabutylammonium chloride, tetrabutylammonium bromide, tetrabutylammonium hydroxide, mixtures thereof and the like.

Suitable phosphonium catalysts include, for example, tetra(hydroxymethyl)phosphonium chloride, tetrahydroxymethylphosphonium bromide, ethyltriphenylphosphonium iodide, butyltriphenylphosphonium halides, methyltriphenylphosphonium halides, tetrabutylphosphonium halides, methyltributylphosphonium halides, ethyltriphenylphosphonium acetate.acetic acid complex, tetrabutylphosphonium acetate.acetic acid complex, mixtures thereof and the like.

Suitable imidazoles which can be employed herein include, for example, 2-methyl imidazole, mixtures thereof and the like.

Suitable mole ratios of aminohydrocarbyl piperazine to urea are from about 1.8:1 to about 6:1, preferably from about 1.8:1 to about 4:1, most preferably from about 1.8:1 to about 2.2:1.

The reaction can be carried out at any suitable temperature which can vary depending upon the specific reactants and catalyst employed. However, generally, temperatures of from about 60° C. to about 185° C., preferably from about 80° C. to about 160° C. and most preferably from about 118° C. to about 135° C. can be employed.

The particular reaction time depends upon the particular reactants, catalyst, reaction temperature and pressure and when significantly short can result in low conversion. Longer reaction times tend to produce products having higher amine hydrogen equivalent weights as determined by titration with HCl using bromthymol blue as the indicator. Usually the time is from about 16 to about 200 hours (57,600–720,000 s), preferably from about 18 to about 67 hours (64,800–241,200 s), and most preferably from about 18 to about 24 hours (64,800–86,400 s).

Although it is not necessary and would result in an additional removal or separation step, the process of the present invention can be conducted in the presence of an inert organic reaction medium such as, for example, water, methanol, ethanol, propanol, butanol, mixtures thereof and the like.

The adducts of the present invention are useful as curing agents for epoxy resins.

Suitable epoxy resins which can be employed include, for example, those disclosed by Lee and Neville in HANDBOOK OF EPOXY RESINS, McGraw-Hill Book Co., 1967; by Dante et al. in U.S. Pat. No. 3,477,990; by Perry in U.S. Pat. No. 3,948,855; by Clarke in U.S. Pat. No. 3,687,397, U.S. Pat. No. 3,687,897, U.S. Pat. No. 3,767,624 and U.S. Pat. No. 3,789,053; all of which are incorporated herein by reference.

The following examples are illustrative of the present invention, but are not to be construed as limiting the scope thereof in any manner.

EXAMPLE 1

To a 1-liter reaction vessel equipped with a stirrer, reflux condenser, temperature control and indicating means was added 516.84 g (4 moles) of aminoethyl piperazine. After raising the temperature to about 120° C., 0.32 g (0.0039 mole) of 2-methylimidazole catalyst was added, immediately followed by the addition of 20 g (0.3 mole) of urea. After reacting for 2 hours at 120° C. while stirring, another 0.32 g (0.0039 mole) of 2-methylimidazole catalyst was added, followed by the addition of 40 g (0.7 moles) of urea. The progress of the reaction was monitored periodically by titration with 1N HCL employing brom thymol blue as an indicator. The titration results after 54.3 hours was the same as that after 17.4 hours at 120° C. The excess aminoethyl piperazine was removed by means of a rotoevaporator at 120° C. and 0.120 mm Hg vacuum (0.120 mm Hg absolute). The product yield was >99% based on urea conversion and 93.3% based on net product weight. The amine hydrogen equivalent weight was determined to be 195.3.

The product was a highly viscous straw colored mass.

EXAMPLES 2–20

All the examples in Table 1 employed either 500 ml, 1 liter or 5 liter 3-necked flask or 4 liter resin kettles. These reaction vessels were stirred at 250 to 500 rpm's using a lab stirring motor with an attached stirring rod and paddles. To each reaction vessel was attached a water cooled condenser, thermometer, temperature controller made by $I^2R$ Thermowatch Instruments, Cheltenham, Pa. and one heat lamp, except for 4 liter sized runs where two heat lamps were used. The heat lamps were controlled using $I^2R$ thermowatch and the lamps were positioned in such a manner as to prevent localized heating on the sides of the vessel.

The liquid aminoethyl piperazine (AEP) was added to the vessel at ambient temperature. The stirrer and $I^2R$ thermowatch were turned on and the AEP was heated to the reaction temperature as given in Table I. Then the solid urea pellets were added in increments of from 3 to 7 additions at approximately equal intervals of time between each addition. For most of the runs given in Table I these increments were of approximately equal amounts.

The reaction conditions for each example are given in Table I. The molar ratio of AEP to urea varied from 1.9/1 to 6.0/1. The reaction temperature varied from 118° C. to 150° C. while the total time required to add the urea incrementally to the AEP varied from 1 to 3.1 hours.

In each example the urea was added manually to the stirred AEP at or near the reaction temperature. Each addition took less than 1 minute (60 s) and the reaction vessel was quickly stoppered after the addition which prevented ammonia from escaping by any route other than through the water cooled condenser. The condenser prevented large quantities of AEP from being lost by entrainment as the ammonia came out. The liberated ammonia was easily detected by holding a stopper wetted with HCl above the condenser which caused white fumes above the condenser. Usually it took from 2 to 5 minutes (120 to 300 s) after the first urea addition before any liberation of ammonia was detectable. Thereafter, the ammonia was continually given off throughout the remaining incremental additions and until the reaction was terminated by turning off the heat source and allowing the product to cool off.

An endotherm usually about 2° C. to 3° C. was always detected with each addition. Each urea addition was accompanied by a considerable frothing of the stirred reactants, due to escaping ammonia.

By adding the urea incrementally, "frothing over" of liquid product was prevented and the intervals of time between additions was adjusted to allow the temperature to return to the desired setting.

Samples were taken periodically and titrated with 1N HCl to a green end point using brom thymol blue indicator. Then the amine equivalent weight was determined by using the formula Amine Equivalent Weight =

$$\frac{\text{Sample Weight (Grams)}}{\text{Titrant (ml)} \times 10^{-3} \text{ (equivalents/ml)}}$$

With this method no distinction was made between a primary and a secondary amine. For example, 2 moles of HCl were required to titrate 1 mole of aminoethyl piperazine.

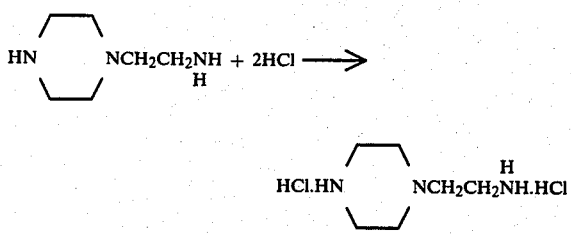

Hence, initially the aminoethyl piperazine before reacting with urea had an amine equivalent weight very close to its molecular weight divided by 2 or 129.21 divided by 2=64.61. For all of these examples, the reaction temperature was maintained and the stirring was continued until the amino equivalent weights as reported in Table II were attained. The amine equivalent weights for these examples ranged from 123 to 207.

Generally for AEP/urea adducts made from AEP/urea molar ratios of 1.9/1 to 2.1/1, the residual AEP was from about 3% to 10%. Residual AEP reduced the viscosity of the hardener and made it easier to mix for curing epoxy resins.

For runs where a considerably higher AEP/urea molar ratio was used the unreacted aminoethyl piperazine was stripped by placing the product solution in a rotaflask. Then the flask was attached to a rotaevaporator using a heat lamp and variac to control the stripping temperature and a vacuum pump was used to reduce the pressure. The stripping temperatures, stripping time and pressure used are given in Table I.

TABLE I

LAB BATCH REACTIONS
General Procedure: Incremental Addition of Urea to Aminoethyl piperazine

| REACTION CONDITIONS | EXAMPLE 2 | EXAMPLE 3 | EXAMPLE 4 | EXAMPLE 5 | EXAMPLE 6 | EXAMPLE 7 | EXAMPLE 8 |
|---|---|---|---|---|---|---|---|
| AEP, g | 2816.78 | 2816.78 | 2816.78 | 2584.2 | 2584.2 | 646.05 | 2816.78 |
| (mole) | (21.8) | (21.8) | (21.8) | (20.0) | (20.0) | (5.0) | (21.8) |
| UREA, g | 688.89 | 688.89 | 688.89 | 632.19 | 632.19 | 150.15 | 654.65 |
| (mole) | (11.47) | (11.47) | (11.47) | (10.526) | (10.526) | (2.5) | (10.9) |
| AEP/UREA (mole ratio) | 1.9/1 | 1.9/1 | 1.9/1 | 1.9/1 | 1.9/1 | 2.0/1 | 2.0/1 |
| CATALYST | None | None | None | 2-methyl imidazole | 2-methyl imidazole | 2-methyl imidazole | None |
| CATALYST AMOUNT (g per mole UREA) | — | — | — | .37 | .37 | .89 | — |
| REACTION TEMP. (°C.) | 135 | 135 | 135 | 120 | 120 | 150 | 135 |
| UREA Add. Time Hours/ (Seconds) | 2.4 (8640) | 2.4 (8640) | 2.4 (8640) | 2.6 (9360) | 2.6 (9360) | 1.6 (5760) | 1.4 (5040) |
| REACTION TIME Hours/ (Seconds) | 22 (79,200) | 45.7 (164,520) | 141.4 (509,040) | 22 (79,200) | 77 (277,200) | 23 (82,800) | 22.4 (80,640) |
| EXCESS AEP STRIPPING CONDITIONS: | | | | | | | |
| Strip temp. (°C.) | N.S.*** | N.S. | N.S. | N.S. | N.S. | N.S. | N.S. |
| Pressure (mmHg) | N.S. | N.S. | N.S. | N.S. | N.S. | N.S. | N.S. |
| Strip time (hrs) | N.S. | N.S. | N.S. | N.S. | N.S. | N.S. | N.S. |
| ANALYSIS: | | | | | | | |
| Amine Equivalent weight | 143.67 | 145.53 | 155.00 | 130.70 | 159.54 | 133.96 | 129.5 |
| Scale of Reactions (gms of Reactants) | 3505.67 | | | | | 798.43 | 3471.43 |
| Yield (gms. Product) | | | | | | 708.20 | |

| REACTION CONDITIONS | EXAMPLE 9 | EXAMPLE 10 | EXAMPLE 11 | EXAMPLE 12 | EXAMPLE 13 | EXAMPLE 14 | EXAMPLE 15 |
|---|---|---|---|---|---|---|---|
| AEP, g | 2816.78 | 2816.78 | 2816.78 | 2816.78 | 2816.78 | 2957.62 | 2957.62 |
| (mole) | (21.8) | (21.8) | (21.8) | (21.8) | (21.8) | (22.89) | (22.89) |
| UREA, g | 654.65 | 654.65 | 654.65 | 654.65 | 654.65 | 654.65 | 654.65 |
| (mole) | (10.9) | (10.9) | (10.9) | (10.9) | (10.9) | (10.9) | (10.9) |
| AEP/UREA (mole ratio) | 2.0/1 | 2.0/1 | 2.0/1 | 2.0/1 | 2.0/1 | 2.1/1 | 2.1/1 |
| CATALYST | None | None | None | None | None | None | None |
| CATALYST AMOUNT (g per mole UREA) | — | — | — | — | — | — | — |
| REACTION TEMP. (°C.) | 135 | 135 | 135 | 120 | 130 | 135 | 135 |
| UREA Add. Time Hours/ (Seconds) | 1.4 (5040) | 1.3 (6080) | 1.4 (5040) | 1.3 (6080) | 1.2 (4320) | 1.4 (5040) | 1.4 (5040) |
| REACTION TIME Hours/ (Seconds) | 47.25 (170,100) | 66.5 (239,400) | 141.5 (509,400) | 90.47 (325,692) | 95 (342,000) | 48.4 (174,240) | 113.4 (408,240) |
| EXCESS AEP STRIPPING CONDITIONS: | | | | | | | |
| Strip temp. (°C.) | N.S. | N.S. | N.S. | N.S. | N.S. | N.S. | N.S. |

TABLE I-continued
LAB BATCH REACTIONS
General Procedure: Incremental Addition of Urea to Aminoethyl piperazine

| | | | | | | | |
|---|---|---|---|---|---|---|---|
| Pressure (mmHg) | N.S. | N.S. | N.S. | N.S. | N.S. | N.S. | N.S. |
| Strip time (hrs) | N.S. | N.S. | N.S. | N.S. | N.S. | N.S. | N.S. |
| ANALYSIS: | | | | | | | |
| Amine Equivalent weight | 135.83 | 132.45 | 137.79 | 130.60 | 132.87 | 128.28 | 130.21 |
| Scale of Reactions (gms of Reactants) | 3471.43 | 3471.43 | 3471.43 | 3471.43 | 3471.43 | — | 3612.27 |
| Yield (gms. Product) | | 3097.0 | 2982.6 | 3107.20 | 3104.50 | | |

| REACTION CONDITIONS | EXAMPLE 16 | EXAMPLE 17 | EXAMPLE 18 | EXAMPLE 19 | EXAMPLE 20 |
|---|---|---|---|---|---|
| AEP, g | 2740.3 | 387.63 | 516.84 | 516.84 | 2609 |
| (mole) | (21.208) | (3.0) | (4.0) | (4.0) | (20.19) |
| UREA, g | 600.6 | 60.06 | 60.06 | 60.06 | 202.12 |
| (mole) | (10.0) | (1.0) | (1.0) | (1.0) | (3.365) |
| AEP/UREA (mole ratio) | 2.12/1 | 3.0/1 | 4.0/1 | 4.0/1 | 6.0/1 |
| CATALYST | None | DOWEX MSA-1 (Cl form) | 2-methyl imidazole | 2-methyl imidazole | 2-methyl imidazole |
| CATALYST AMOUNT (g per mole UREA) | — | 49.74 | .64 | .32 | 1.0 |
| REACTION TEMP. (°C.) | 120 | 120 | 118 | 120 | 120 |
| UREA Add. Time Hours/(Seconds) | 1.0 (3600) | 2.3 (8280) | 2.2 (7920) | 3.1 (11,160) | 1.9 (6840) |
| REACTION TIME Hours/(Seconds) | 118 (424,800) | 22.7 (81,720) | 54.3 (195,480) | 26.5 (95,400) | 107 (385,200) |
| EXCESS AEP STRIPPING CONDITIONS: | | | | | |
| Strip temp. (°C.) | N.S. | 160 | 125 | 120 | 125 |
| Pressure (mmHg) | N.S. | .15 | .15 | .05 | .10 |
| Strip time (hrs) | N.S. | 4.0 | 24.2 | ~4 | 3.7 |
| ANALYSIS: | | | | | |
| Amine Equivalent weight | 123.26 | 207.28 | 195.31 | 156.42 | 183.06 |
| Scale of Reactions (gms of Reactants) | 3340.9 | 447.69 | 577.54 | 577.22 | 2814.49 |
| Yield (gms. Product) | 3000.1 | — | 215.97* | 542.30** | 2671.8** |

*Net wt. of stripped product
**Net wt. after reaction and before stripping
***N.S. = not stripped

EXAMPLE 21

To a 4 liter resin kettle equipped with a water cooled condenser, mechanical stirrer, thermometer, temperature controller and heat lamps was added 2480.83 grams (19.2 moles) aminoethylpiperazine (AEP). After heating to 120° C. and switch stirring was added 3.55 grams (0.0432 moles) of 2-methyl imidazole. When the temperature once again reached 120° C., 127 grams (2.11 moles) of urea was added over a 1 minute (60 s) period. During this time the temperature cooled down to 112° C. After 10 minutes (600 s), 353.48 grams (5.89 moles) urea was added over a 4 minute (240 s) period. The flask temperature was 122° C. and during the addition the flask cooled to 112° C. due to ammonia being liberated.

The reaction temperature rose to 120° C. in 53 minutes (3180 s) after the last urea addition and this reaction temperature was maintained for 71 hours (255,600 s) addition hours. Then a reaction temperature of 123° C. to 125° C. was maintained for 23.75 hours (85,392 s). Then the reaction was cooled down. A mass balance for this reaction gave 2695.3 grams. The ammonia weight loss was 269.56 grams (15.86 moles). The expected ammonia weight loss for 100% conversion to pure bis aminoethylpiperazine/urea adduct of n=0 was 272 grams (16 moles) which corresponds to a loss of 2 moles NH$_3$ for each 1 mole of urea. This translates into a yield of 99.10%. A sample was titrated with 1N HCl using bromthymol blue indicator and found to have an amine equivalent weight equal to 111.33. The product was a reddish-brown liquid which had a significantly lower viscosity due to using an excess of greater than 2 moles AEP per 1 mole urea. Initially this run used 19.2 moles AEP to 8 moles urea which equals a 2.4/1 molar ratio. This product was analyzed by liquid chromatography which confirmed the presence of residual AEP and also confirmed that essentially all the urea had reacted since only trace amounts were detectable. This was also confirmed by infrared and gel permeation chromatography. Analysis of this liquid product by NMR (nuclear magnetic resonance) analysis supports the presence of mostly disubstituted urea and some multisubstituted urea components.

EXAMPLE 22

A net weight of 339.3 grams of product from the above example was placed in a 1-neck one liter flask. The flask was then attached to a rotary evaporator and the residual aminoethylpiperazine was removed at 65° C. to 105° C. while using a vacuum pump to reduce the pressure to about 3.5 mm of Hg absolute pressure at the start of stripping to about 0.05 mm of Hg toward the end of stripping. The total stripping time was 95 minutes (5700 s). A net weight of 226.9 grams of a medium red viscous liquid (at ambient temperature) was obtained. Analysis by nuclear magnetic resonance and infrared strongly supported the reaction product as being a bis AEP/urea adduct of n=0 and n=1. The sample was titrated with 1N NCl using bromthymol blue indicator and found to have an amine equivalent weight of 133.07.

EXAMPLE 23

To a disposable beaker was added 60.16 grams (0.32 equiv.) of a diglycidyl ether of bisphenol A having an EEW of 188 which had been preheated to a temperature of 60° C. and 35.62 grams (0.32 equiv.) of the adduct prepared in Example 21 which had an amine equivalent weight of 111.33 and had also been preheated to a temperature of 60° C. After about 2 minutes (180 s) of mixing, the mixture began to exotherm and was quickly poured into a sheet mold. The mold was placed in an oven and cured at 60° C. for 2 hours (7200 s), then at 40° C. for 45 minutes (2700 s) and finally at 96° C. for 2 hours (7200 s).

The resultant cured polymer was very tough and could not easily be broken by hand bending. The molded product was non-tacky when touched which indicated relatively complete curing has been obtained. A portion of the cured product was analyzed on a Perkins Elmer Thermomechanical Analyzer which indicated that the Tg (glass transition temperature) of the product was 101° C.

EXAMPLE 24

To a disposable beaker was added 39.9 grams (0.3 equivalents) of the adduct prepared in Example 22 and 56.4 grams (0.30 equivalent) of a diglycidyl ether of bispheol A having an average EEW of 188. This mixture was hand mixed at room temperature for 4 minutes (240 s) and poured into a mold for making stick specimens of ½"×½"×8" (1.27 cm.×1.27 cm.×20.32 cm.). The mold was left at room temperature (25° C.) for 50 hours (180,000 s). The sticks were non-tacky and had a smooth surface. Three of the sticks were post cured at 94° C. for 2¼ hours (135 s). The izod impact determined on a 4" section of one of the post cured sticks was >2 ft-lbs. The heat distortion temperature of one of the sticks placed in an oil bath heated at a rate of 6° F./minute (0.05° C./s) was 177° F. (80.6° C.).

EXAMPLE 25

In a suitable mixing container was added 92.48 g of a bis aminoethylpiperazine/urea (bis AEP/urea) adduct prepared as in Example 21 and warmed to a temperature of 60° C. and then 186 g of a diglycidyl ether of bisphenol A having an epoxide equivalent weight of 186 was added. The components were mixed well and poured onto a sheet mold. The mold was heated at 100° C. for 2 hours (7200 s) and then at 150° C. for an additional 2 hours (7200 s).

In a similar manner, the epoxy resin was cured with aminoethylpiperazine (AEP) and also triethylenetetramine (TETA) for comparative purposes. The results are given in the following Table II.

TABLE II

|  | Bis AEP*/Urea | AEP | TETA** |
|---|---|---|---|
| Tensile strength, psi | 10,099 | 10,227 | 11,587 |
| MPa | 69.6 | 70.5 | 79.8 |
| Tensile modulus, psi | $3.53 \times 10^5$ | $3.025 \times 10^4$ | $3.79 \times 10^5$ |
| kPa | $24.339 \times 10^5$ | $20.857 \times 10^4$ | $26.131 \times 10^5$ |
| Flexural strength, psi | 18,221 | 18,466 | 20,770 |
| MPa | 125.5 | 127.2 | 143.1 |
| Flexural modulus, psi | $4.87 \times 10^5$ | $4.11 \times 10^5$ | $4.89 \times 10^5$ |
| kPa | $33.58 \times 10^5$ | $28.34 \times 10^5$ | $33.72 \times 10^5$ |
| Elongation (%) | 12.7 | 12.2 | 8.45 |
| Glass Transition (°C.) | 105 | 112 | 113 |
| Izod Impact (Ft-lb/inch) | >2 | 1.8 | 0.4 |
| Barcol Hardness | 33 | 26 | 36.3 |

*AEP = aminoethylpiperazine
**TETA = triethylenetetramine

We claim:

1. An uncrystallized reaction product of (A) at least one aminohydrocarbyl piperazine and (B) urea in a molar ratio of (A) to (B) of from about 1.8:1 to about 8:1.

2. An uncrystallized reaction product of claim 1 wherein the molar ratio of (A) to (B) is from about 1.8:1 to about 4:1.

3. An uncrystallized reaction product of claim 2 wherein the molar ratio of (A) to (B) is from about 1.8:1 to about 2.2:1.

4. An uncrystallized reaction product of claims 1, 2 or 3 wherein component A is represented by the general formula

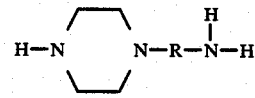

wherein R is a divalent hydrocarbyl group having from about 2 to about 10 carbon atoms.

5. An uncrystallized reaction product of claim 4 wherein R has from about 2 to about 4 carbon atoms.

6. An uncrystallized reaction product of claim 4 wherein R has from about 2 to about 3 carbon atoms.

7. An uncrystallized reaction product of claims 1, 2 or 3 wherein component (A) is aminoethyl piperazine, aminopropyl piperazine, aminobutyl piperazine, aminopentyl piperazine, or mixture thereof.

8. An uncrystallized reaction product of claim 7 wherein component (A) is aminoethyl piperazine.

9. An aminohydrocarbyl piperazine-urea adduct represented by the formula

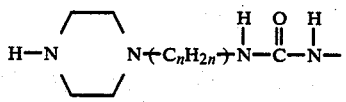

-continued
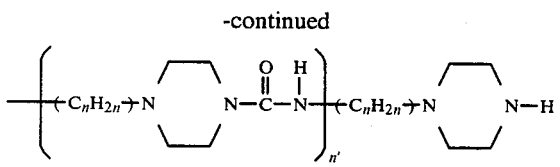
wherein each n is independently an integer from 2 to about 10 and n' has an average value of from about zero to about 2.
10. An adduct of claim 9 wherein each n is independently an integer from about 2 to about 4.
11. An adduct of claim 9 wherein n is an integer from about 2 to about 3.
* * * * *